United States Patent [19]

Hammer et al.

[11] 4,354,960

[45] Oct. 19, 1982

[54] PROCESS FOR THE PRODUCTION OF BORON-CONTAINING NICKEL-ALUMINUM OXIDE CATALYSTS

[76] Inventors: Hans Hammer, An Adamshäuschen 3; Heinz Jacobi, Jacobstr. 184, both of 5100 Aachen, Fed. Rep. of Germany

[21] Appl. No.: 126,825

[22] Filed: Mar. 3, 1980

[30] Foreign Application Priority Data

Mar. 1, 1979 [DE] Fed. Rep. of Germany ....... 2907943

[51] Int. Cl.$^3$ ............................................. B01J 21/02
[52] U.S. Cl. .................................................... 252/432
[58] Field of Search ......................................... 252/432

[56] References Cited

U.S. PATENT DOCUMENTS 2,927,086  3/1960  Gordon et al. ...................... 252/432
2,963,459  12/1960  Nicholson et al. .............. 252/432 X
3,210,157  10/1965  Lewis et al. ...................... 252/432 X
3,547,830  12/1970  Shropshire .......................... 252/432
3,869,521  3/1975  Benson ............................. 252/432 X

*Primary Examiner*—Delbert E. Gantz
*Assistant Examiner*—William G. Wright
*Attorney, Agent, or Firm*—Michael J. Striker

[57] ABSTRACT

Process for the production of boron-containing nickel-aluminum oxide catalysts. Solutions containing nickel and aluminum are reacted with aqueous sodium borohydride. Precipitation occurs, followed by drying and compressing the resultant precipitate into catalyst shapes. The precipitation may occur in the presence of metallic promoter salts. The catalysts are used for the methanization of carbon monoxide by hydrogen. Good results and long catalyst life are furthered by methanizing a mixture of $H_2$:CO of about 3:1 by volume, at an operating pressure between about 40–45 bar, and a spatial velocity between about $2 \times 10^4$ to $10^5 h^{-1}$.

9 Claims, No Drawings

PROCESS FOR THE PRODUCTION OF BORON-CONTAINING NICKEL-ALUMINUM OXIDE CATALYSTS

BACKGROUND OF THE INVENTION

Process for the production of boron-containing nickel-aluminum oxide catalysts

It is known how to implement hydration of carbon monoxide to methane by means of hydrogen in the presence of nickel-containing catalysts. These nickel catalysts are produced with or without carrier substances such as, for instance, aluminum oxide, silicon oxide or titanium oxide, and with, or without, promoter metals such as, for instance, tungsten, molybdenum, chromium, magnesium or uranium. These catalysts are, however, of the disadvantage that the Boudard reaction, occurring as secondary reaction, will cause carbon deposition on the catalysts and thus their deactivation. This deposition of carbon may be prevented only by a measure impairing methanization, for instance by selecting a low reaction temperature, using a synthesis gas mixture of a ratio $H_2:CO_2 > 3:1$, or by using a gas mixture with a high $CO_2/CO$ ratio.

SUMMARY OF THE INVENTION

It has been found that boron-containing nickel-aluminum oxide catalysts will have longer life in the hydration of carbon monoxide to methane, if their components were compounded by simultaneous precipitation. Correspondingly, the catalysts as per invention are produced by reacting solutions containing nickel or aluminum, with aqueous sodiumborohydride and transforming the resultant precipitation into catalyst shapes by drying and compressing. Precipitation of the catalyst may, herein, also be effected in the presence of the initially named metallic promoters, so that certain further increases in the activity of the catalysts as per invention may be achieved.

Concentrations of solutions coming into consideration for the production of catalysts as per invention, and quantity ratios between solutions are to be selected in such a manner that the dried catalyst will contain approximately 60-90 parts by weight nickel, 5-30 parts by weight aluminum, and 5-10 parts by weight boron. The aforenoted metallic promotors may be contained in quantities up to approximately 2%—all quantities relative to metals.

The precipitated nickel will be contained in the dried catalyst partly as oxide and partly as finely distributed metal. Aluminum is contained as, respectively, $Al_2O_3$ or Aluminum oxide hydrate, and boron as nickel boride and boric acid. In the course of its application as hydration catalyst, virtually all nickel will be reduced to metallic nickel, whilst the boron in the nickel boride will in its major part be converted into boric acid by hydrolysis effected by the water vapor originating from methanization of CO, and evaporated from the contact in this form. The pore formation in the catalyst thus brought about will considerably increase the activity of the catalyst during hydration.

Mixtures of 10% alcoholic solutions of nickel and aluminum salts, reacted with 10% aqueous solutions of sodiumborohydride will suitably serve as initial solution. Depending upon the solubility of the initially used salts—and any solvents, water excepted, come into consideration herein,—solutions may be selected also of a higher or lower concentration than above.

Promoter metals may be added to an aluminum or nickel solution either as aqueous solution or dissolved in an organic solvent, with preferably Mg, Ba, Cu, Fe, Cr, Mn added as nitrates, V as ammonium vanadate, Mo as ammonium molybdate, Sr as chloride and Ca as acetate.

The new simultaneously precipitated catalysts have the advantage of being highly active and selective. In comparison with the production of known nickel catalysts, their production is more simple and of improved repeatability. Simultaneously precipitated catalysts lend themselves with facility to processing into catalyst shapes by pressing. Surprisingly, they may furthermore be subjected to permanent thermal loads of 500° to 550° C., temporarily up to 700° C., without their activity being impaired.

The useful life of the catalyst, $t_{St}$ will be $>700$ operating hours, provided the content of catalyst poisons ($H_2S$, etc.) will be below 1 ppm, provided methanization of a mixture $H_2:CO$ of about 3:1 by volume taking place, provided this mixture having a spatial velocity of approx. $2 \times 10^4$ to $10^5 h^{-1}$, and at an operating pressure of about 40-45 bar with a reaction of carbon monoxide to methane of more than 90%. Activity of the catalysts may be reduced if desired for better control of the resulting reactive heat, by an increase of their aluminum content.

Further advantages are their simple activation and good handling. The new catalysts are not pyrophorous.

Activation of the catalysts is preferably effected by means of a hydrogen stream at 1-50 bar, preferably 20-30 bar, and at 300°-400° C.

Since methanization of synthesis gases will ensue under similar conditions, the catalysts may be used for the methanizing process also without previous separate activation.

Production of the catalysts as per invention, and the results of their application in methanizing gases containing $H_2$ and CO in a ratio of $H_2:CO$ about 3:1, shall be explained more closely using the following embodiments.

The novel features which are considered as characteristic for the invention are set forth in particular in the appended claims. The invention itself, however, both as to its construction and its method of operation, together with additional objects and advantages thereof, will be best understood from the following description of specific embodiments.

DESCRIPTION OF THE PREFERRED EMBODIMENTS

Example 1

A mixture of a respective methanolic solution of nickel nitrate and aluminum nitrate of 10% by weight with a mixture ratio of 2:1, is cooled to 0° C. and precipitated whilst being strongly agitated and mixed with an aqueous sodiumborohydride solution of 10% by weight, using herein a quantity of sodiumborohydride of a 1:3 weight ratio to the quantity of nickel nitrate as used. During precipitating, a pH value of pH 7 to pH 10, preferably pH 9 to pH 9.5 is maintained. The reactive heat generated on precipitation is dissipated by evaporation of the solvent. The precipitate is filtered off and eluted with a quantity of water and methanol corresponding to the respective volume of the previously used solvent. The catalyst thus obtained is dried for 24 h at 0.05 bar and at temperatures of 50° to 300° C., preferably 90° to 110° C. After reduction in size to a particle size of <100 μm and pelletizing under a pressure of $10^4$ bar to $4 \times 10^4$ bar, preferably at a pressure of $10^4$ bar to $1.3 \times 10^4$ bar, the catalyst shapes are activated in a hydrogen stream at temperatures from 300° to 400° C. and hydrogen partial pressures between 1 and 50 bar, preferably at a hydrogen partial pressure of 20 to 30 bar.

If a gas mixture of the composition
    hydrogen: 74.3% by vol.
    carbon monoxide: 25.7% by vol.
is used with a catalyst produced as described afore, methanization at an operating pressure of 41 bar, a spatial velocity of approx. 32,000 $h^{-1}$ will yield a reaction of carbon monoxide to methane of 94.9%, and a reaction of carbon monoxide to carbon dioxide of 3.3%, whilst 1.8% of carbon monoxide are not being reacted.

Example 2

A mixture of a respective, 10% by weight, methanolic solution of nickel nitrate, aluminum nitrate and magnesium nitrate (promotor), at a weight ratio of 2:1:0.2, is cooled to 0° C. and precipitated under strong agitation and mixing with a 10% by weight aqueous solution of sodiumborohydride, using herein a quantity of sodiumborohydride having a weight ratio of 1:3 relative to the quantity of nickel nitrate as used. A pH value of 7 to 10, preferably 9 to 9.5 is maintained during precipitation. Further processing including activation is effected as described in Example 1. If this catalyst is used for methanization of a gas mixture of
    hydrogen: 77.5% by vol.
    carbon monoxide: 22.5% by vol.
at an operating pressure of 42 bar and a spatial velocity of 21,000 $h^{-1}$, a reaction of carbon monoxide to methane will yield 92.3% and a reaction of carbon monoxide to carbon dioxide will yield 2.5% whilst 3.3% of carbon monoxide are not being reacted.

Example 3

A mixture of a respective, 10% by weight, methanolic solution of nickel nitrate and aluminum nitrate, at a weight ratio of 2:1, is cooled to 0° C. and precipitated under strong agitation and mixing with a mixture of aqueous, 10% by weight, solutions of sodiumborohydride and sodium tungstate (promoter metal) of a ratio of 2:1 by weight, wherein the quantities of the sodiumborohydride and nickelnitrate should be in a weight ratio of 1:3. A pH value of pH 7 to pH 10, preferably pH 9 to pH 9.5 is maintained during precipitation. Further processing, including activation, is effected as per Example 1.

If this catalyst is used for the methanization of a gas mixture of
    hydrogen: 71.5% by vol.
    carbon monoxide: 28.5% by vol.
at an operating pressure of 41 bar and a spatial velocity of approx. 50,000 $h^{-1}$, a reaction of carbon monoxide to methane will yield 93.3%, and of carbon monoxide to carbon dioxide 3.7%, whilst 3.0% of the carbon monoxide will not be reacted.

It will be understood that each of the elements described above, or two or more together, may also find a useful application in other types of methods for producing and using catalysts differing from the types described above.

While the invention has been illustrated and described as embodied in a process for the production and use of boron-containing nickel-aluminum oxide catalysts, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

We claim:

1. A process for the production of boron-containing nickel-aluminum oxide catalysts, comprising the steps of reacting solutions containing nickel and aluminum, with aqueous sodium borohydride and forming a precipitate while cooling to about 0° C., and maintaining a pH value of about 7 to 10, and drying and compressing the resultant precipitate into catalyst shapes.

2. The process of claim 1, wherein said precipitation takes place in the presence of metallic promoter salts.

3. The process of claim 2, wherein said metallic promoter salts are salts of tungsten, molybdenum, chromium, magnesium, uranium, barium, copper, iron, manganese, vanadium, strontium or calcium.

4. The process of claim 2, wherein said metallic promoter salts are present in the dried catalyst in quantities up to about 2% by weight relative to the metals.

5. The process of claim 1, wherein during precipitation a pH value of about 9 to 9.5 is maintained.

6. The process of claim 1, further comprising activating said catalysts by means of a hydrogen stream at 1–50 bar and at 300°–400° C.

7. The process of claim 6, wherein said activating occurs at pressure between about 20–30 bar.

8. A catalyst for the methanization of carbon monoxide by hydrogen, produced according to claim 1, comprising 60–90 parts by weight nickel, 5–30 parts by weight aluminum and 5–10 parts by weight boron.

9. The catalyst of claim 8, in the form of pellets made of particles of a size less than about 100 μm.

* * * * *